US010881598B2

(12) United States Patent
Edmiston et al.

(10) Patent No.: US 10,881,598 B2
(45) Date of Patent: Jan. 5, 2021

(54) METHOD OF USING PERSONAL AND HOME CARE COMPOSITIONS CONTAINING A SOL-GEL DERIVED MATERIAL

(71) Applicant: ABS MATERIALS, INC., Wooster, OH (US)

(72) Inventors: Paul L. Edmiston, Wooster, OH (US); Stacey L. Dean, Broadview Heights, OH (US)

(73) Assignee: ABS MATERIALS, INC., Wooster, OH (US)

( * ) Notice: Subject to any disclaimer, the term of this patent is extended or adjusted under 35 U.S.C. 154(b) by 54 days.

(21) Appl. No.: 16/110,837

(22) Filed: Aug. 23, 2018

(65) Prior Publication Data

US 2018/0360718 A1 Dec. 20, 2018

Related U.S. Application Data

(62) Division of application No. 15/148,984, filed on May 6, 2016, now abandoned.

(60) Provisional application No. 62/157,929, filed on May 6, 2015.

(51) Int. Cl.
| | | |
|---|---|---|
| *C11D 9/36* | (2006.01) | |
| *A61K 8/58* | (2006.01) | |
| *A61Q 19/00* | (2006.01) | |
| *A61K 8/04* | (2006.01) | |
| *A61Q 5/02* | (2006.01) | |
| *A61Q 19/10* | (2006.01) | |

(52) U.S. Cl.
CPC .............. *A61K 8/585* (2013.01); *A61K 8/042* (2013.01); *A61Q 5/02* (2013.01); *A61Q 19/008* (2013.01); *A61Q 19/10* (2013.01)

(58) Field of Classification Search
CPC ....... C11D 3/0094; C11D 3/162; C11D 3/373; C11D 9/36
See application file for complete search history.

(56) References Cited

U.S. PATENT DOCUMENTS

| | | |
|---|---|---|
| 2,798,053 A | 7/1957 | Brown |
| 3,755,560 A | 8/1973 | Dickert et al. |
| 4,421,769 A | 12/1983 | Dixon et al. |
| 4,509,949 A | 4/1985 | Huang et al. |
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 5,011,681 A | 4/1991 | Ciotti et al. |
| 5,087,445 A | 2/1992 | Haffey et al. |
| 5,100,660 A | 3/1992 | Hawe et al. |
| 7,790,830 B2 | 9/2010 | Edmiston |
| 8,563,649 B2 | 10/2013 | Edmiston |
| 2013/0026093 A1* | 1/2013 | Yang ........................ C02F 1/288 210/602 |
| 2013/0029843 A1* | 1/2013 | Edmiston ........... B01J 20/28076 502/401 |
| 2013/0292620 A1* | 11/2013 | Edmiston .................. B66F 3/24 254/93 R |
| 2014/0374350 A1* | 12/2014 | Yang .................... B01J 20/0229 210/635 |
| 2015/0342868 A1 | 12/2015 | Greaves | |

OTHER PUBLICATIONS

CTFA International Cosmetic Ingredient Dictionary, 4th Edition, 1991, pp. 12 and 80.
CTFA International Cosmetic Ingredient Dictionary and Handbook, 10th Edition, 2004, vol. 3, pp. 2112-2115, 2144-2145, 2178-2179, 2182-2185, 2192-2197, 2204-2215, 2228-2229, 2234-2267, 2292-2293.
CTFA International Cosmetic Ingredient Dictionary and Handbook, 12th Edition, 2008, vol. 3, pp. 3013, 3076-3079, 3114, 3151, 3153-3154, 3159-3164, 3173-3176, 3186-3200, 3216-3218, 3223-3267, 3271-3273, 3302-3303.
Stewart, M.E., Semin. Dermatol. 11, 100-105 (1992).
McCutcheon's emulsifiers & detergents. (1986), pp. 63-292, Glen Rock, N.J: McCutcheon's Division, MC Pub. Co.

* cited by examiner

*Primary Examiner* — Charles I Boyer
(74) *Attorney, Agent, or Firm* — Arent Fox LLP

(57) ABSTRACT

Disclosed is a method for removing fatty oil from a surface containing the fatty oil comprising the steps of applying to the surface containing the fatty oil a composition comprising a sol-gel derived material, the sol-gel derived material including a plurality of alkylsiloxy substituents and the sol-gel derived material obtained from
(a) at least one first alkoxysilane precursor having the formula:

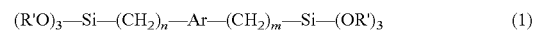

$$(R'O)_3\text{—Si—}(CH_2)_n\text{—Ar—}(CH_2)_m\text{—Si—}(OR')_3 \quad (1)$$

where n and m are individually an integer from 1 to 8, Ar is a single-, fused-, or poly-aromatic ring, and each R' is independently a $C_1$ to $C_5$ alkyl group and
(b) optionally, at least one second precursor having the formula:

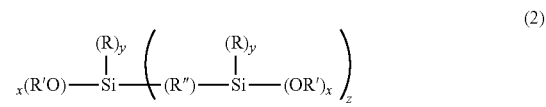

where x is 1, 2, 3 or 4; y is 0, 1, 2, 3; z is 0, 1; the total of x+y+z is 4; each R is independently an organic functional group; each an R' is independently a $C_1$ to $C_5$ alkyl group and R" is an organic bridging group and then moving the composition from the surface to remove the fatty oil.

20 Claims, 1 Drawing Sheet

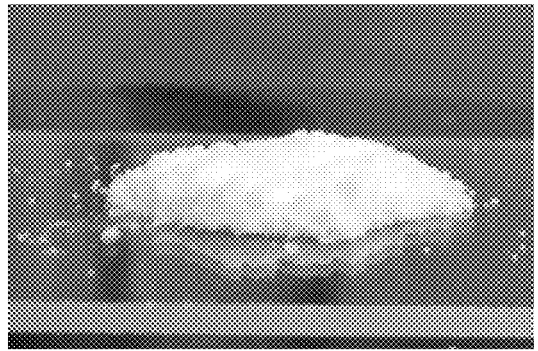 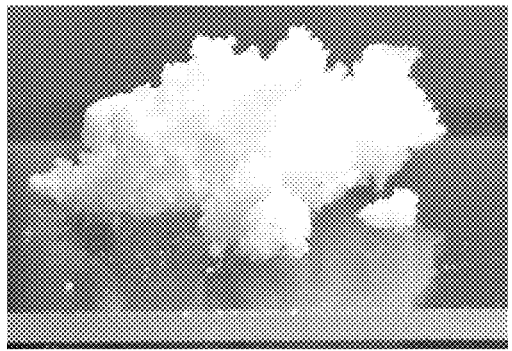
Osorb sorbent (left) before and (right) after exposure to artificial sebum.

METHOD OF USING PERSONAL AND HOME CARE COMPOSITIONS CONTAINING A SOL-GEL DERIVED MATERIAL

CROSS-REFERENCE TO RELATED APPLICATIONS

This application claims priority to U.S. Non-Provisional patent application Ser. No. 15/148,984, filed May 6, 2016, entitled "METHOD OF USING PERSONAL AND HOME CARE COMPOSITIONS CONTAINING A SOL-GEL DERIVED MATERIAL," currently pending, which claims priority to U.S. Provisional Patent Application Ser. No. 62/157,929, filed May 6, 2015, entitled "PERSONAL AND HOME CARE COMPOSITIONS CONTAINING A SOL-GEL DERIVED MATERIAL AND METHOD OF USING SAME," all of which are expressly incorporated by reference herein in their entirety.

BACKGROUND

1. Field of the Invention

The present invention relates generally to the chemical arts. More particularly, the invention relates to a method of using personal care compositions, home care compositions and the like to remove excess fatty oils from a surface.

2. Discussion of Related Art

Sebum is a natural product from the sebaceous gland which, together with sweat produced by the eccrine or aprocrine glands, constitutes a natural moisturizer for the epidermis of the skin. It is reported that the sebaceous gland produces squalene, triglycerides, aliphatic waxes, cholesterol waxes and possibly free cholesterol (Stewart, M. E., Semin. Dermatol. 11, 100-105 (1992)). There is a long felt need for personal care compositions, home care compositions and the like effective in removing excess sebum and other fatty oils from surfaces, including the surfaces of skin, hair, lips and the like.

SUMMARY OF THE INVENTION

Now, in accordance with one aspect of the invention, there has been discovered a method that solves this and related needs. In one aspect, fatty oils are removed from a surface containing a fatty oil by a method comprising the steps of applying to the surface containing the fatty oil a composition comprising a sol-gel derived material, the sol-gel derived material including a plurality of alkylsiloxy substituents and the sol-gel derived material obtained from (a) at least one first alkoxysilane precursor having the formula:

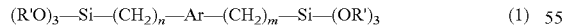

$$(R'O)_3\text{—Si—}(CH_2)_n\text{—Ar—}(CH_2)_m\text{—Si—}(OR')_3 \quad (1)$$

where n and m are individually an integer from 1 to 8, Ar is a single-, fused-, or poly-aromatic ring, and each R' is independently a $C_1$ to $C_5$ alkyl group and (b) optionally, at least one second precursor having the formula:

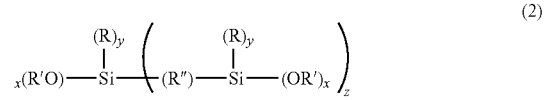

$$(2)$$

$$_x(R'O)\text{—Si}\underset{(R)_y}{\overset{(R)_y}{|}}\!\!\left(\!\!(R'')\text{—Si}\underset{}{\overset{(R)_y}{|}}(OR')_x\!\!\right)_z$$

where x is 1, 2, 3 or 4; y is 0, 1, 2, 3; z is 0, 1; the total of x+y+z is 4; each R is independently an organic functional group; each an R' is independently a $C_1$ to $C_5$ alkyl group and R" is an organic bridging group and then moving the composition from the surface to remove the fatty oil.

In one aspect, the fatty oil is sebum. And in one aspect, the surface includes, without limitation, the surface of skin, hair, or lips.

In one aspect, the composition further comprises a vehicle for the sol-gel derived material. And in one aspect, the composition is a personal care composition or a home care composition.

In one aspect, x is 2 or 3, y is 1 or 2 and z is 0 and R' is a methyl, an ethyl, or a propyl group. In another aspect, R comprises an unsubstituted or substituted straight-chain hydrocarbon group, branched-chain hydrocarbon group, cyclic hydrocarbon group, or aromatic hydrocarbon group.

In one aspect, the plurality of alkylsiloxy groups have the formula:

$$\text{—}(O)_w\text{—Si—}(R_1)_{4-w} \quad (3)$$

where each $R_1$ is independently an organic group as described above and w is an integer from 1 to 3. In another aspect, the first alkoxysilane precursor comprises a bis(trialkoxysilylalkyl)benzene, including without limitation, .bis 1,4-bis(trimethoxysilylmethyl)benzene (BTMB), bis(triethoxysilylethyl)benzene (BTEB), or mixtures thereof. And in one aspect, the second alkoxysilane precursor comprises tetramethoxysilane, methyltrimethoxysilane, methyltriethoxysilane, dimethyldimethoxysilane, dimethyldiethoxysilane, phenyltrimethoxysiliane, aminopropyltrimethoxysilane, 1,4-bis(triethoxysilyl)benzene, 2-(trimethoxysilylethyl)pyridine, bis(triethoxysilylpropyl)amine, para-trifluoromethylterafluorophenyltrimethoxysilane, (tridecafluoro-1,1,2,2-tetrahydro-octyl)trimethoxysilane, 3-aminopropyltrimethoxysilane, 3-mercaptopropyltrimethoxysilane, 3-cyanopropyltrimethoxysilane, 3-sulfoxypropyltrimethoxysilane, isocyanopropyltrimethoxysilane, 2-(3,4-epoxycyclohexyl)ethyltrimethoxysilane, isocyanopropyltrimethoxysilane and trimethoxypropylbenzylcarbamate.

BRIEF DESCRIPTION OF THE DRAWINGS

The following photograph forms part of the present specification and is included to further demonstrate certain aspects of the present disclosure. The disclosure may be better understood by reference to the photograph in combination with the detailed description of specific embodiments presented herein FIG. 1 is a photograph showing the capture of artificial sebum using powdered Osorb sorbent.

DETAILED DESCRIPTION OF THE PREFERRED EMBODIMENTS

Particular embodiments of the invention are described below in considerable detail for the purpose of illustrating its principles and operation. However, various modifications may be made, and the scope of the invention is not limited to the exemplary embodiments described below.

Unless otherwise described, all technical terms used herein have the same meaning as commonly understood by one of ordinary skill in the art to which the present invention pertains. As used herein, "topical application" means to apply or spread a composition onto a surface.

As used herein, the term "effective amount" means an amount effective to accomplish a desired, expected, or intended result, such to remove excess sebum and other fatty residues from a surface.

As used herein "sorb" means to take up whether by adsorption, absorption, sequestration or a combination thereof.

As used herein "swell" means the volume of solvent absorbed per mass of dry sol-gel derived composition As used herein, "swellable" means absorbs at least 1.5 the volume of acetone per mass of the dry sol-gel derived composition, when placed in excess acetone.

As used herein, "nanoparticle" means a particle sized between about 0.05 and about 50 nanometers in one dimension.

In accordance with one aspect of the invention, there has been discovered a method for removing fatty oil from a surface containing the fatty oil comprising the steps of applying to a surface containing a fatty oil a composition comprising an effective amount of a suitable sol-gel derived composition and then moving the composition from the surface to remove the fatty oil. In one aspect of the invention, the sol gel-derived compositions are highly porous materials with high capacity for hydrophobic species. Furthermore, the sol-gel compositions are swellable up to about eight to ten times per mass of the dry sol-gel derived composition, when placed in excess acetone. Sol-gel compositions useful in accordance with the invention are described in U.S. Pat. No. 7,790,830 and U.S. Publ. Patent Appl. No. 2013-0029843, which are herein incorporated by reference, and include OSORB media available from ABS Materials, Wooster, Ohio.

In one aspect, the sol-gel derived material is obtained from at least one first alkoxysilane precursor having the formula:

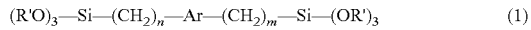

(R'O)$_3$—Si—(CH$_2$)$_n$—Ar—(CH$_2$)$_m$—Si—(OR')$_3$      (1)

where n and m are individually an integer from 1 to 8, Ar is a single-, fused-, or poly-aromatic ring, such as a phenyl or naphthyl ring, and each R' is independently an alkyl group, such as a C$_1$ to C5 alkyl group including, without limitation, methyl, ethyl or propyl groups.

Exemplary first alkoxysilane precursors include, without limitation, bis(trialkoxysilylalkyl)benzenes, such as 1,4-bis(trimethoxysilylmethyl)benzene (BTMB), bis(triethoxysilylethyl)benzene (BTEB), and mixtures thereof, with bis(triethoxysilyl ethyl)benzene being preferred.

In another aspect, the sol-gel derived material is obtained from a mixture of the at least one first alkoxysilane precursor and at least one second alkoxysilane precursor, where the at least one second alkoxysilane precursor has the formula:

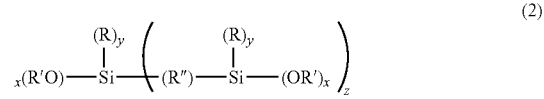

(2)

where x is 1, 2, 3 or 4; y is 0, 1, 2, 3; z is 0, 1; where the total of x+y+z is 4; R is independently an organic functional group; R' is independently an alkyl group as defined above and R" is an organic bridging group, for example an alkyl or aromatic bridging group.

In some embodiments, each R is independently an aliphatic or non-aliphatic hydrocarbon containing up to about 30 carbons, with or without one or more hetero atoms (e.g., sulfur, oxygen, nitrogen, phosphorous, and halogen atoms) or hetero atom containing moieties. Representative R's include straight-chain hydrocarbons, branched-chain hydrocarbons, cyclic hydrocarbons, and aromatic hydrocarbons and are unsubstituted or substituted. In some aspects, R includes alkyl hydrocarbons, such as C$_1$-C$_3$ alkyls, and aromatic hydrocarbons, such as phenyl, and aromatic hydrocarbons substituted with heteroatom containing moieties, such —OH, —SH, —NH$_2$, and aromatic amines, such as pyridine.

Representative substituents for R include primary amines, such as aminopropyl, secondary amines, such as bis(triethoxysilylpropyl)amine, tertiary amines, thiols, such as mercaptopropyl, isocyanates, such as isocyanopropyl, carbamates, such as propylbenzylcarbamate, alcohols, alkenes, pyridine, halogens, halogenated hydrocarbons or combinations thereof.

In certain aspects, the second alkoxysilane precursor can be selected to produce sol-gel compositions that are substantially porous having a dry state pore volume of >0.20 mL/g with pore diameters of 6 to 80 nm as measured by the BET/BJH method, absorb at least ten times the volume of acetone per mass of dry sol-gel derived composition and generate a force upon swelling that is greater than 200 N/g as measured by swelling with acetone in a confined system.

Examples of suitable second precursors include, without limitation, dimethyldimethoxysilane, (4-ethylbenzyl)trimethoxysilane, 1,6-bis(trimethoxysilyl)hexane, 1,4-bis(trimethoxysilyl)benzene, tetramethoxysilane, methyltrimethoxysilane, methyltriethoxysilane, phenyltrimethoxysilane, with dimethyldimethoxysilane, (4-ethylbenzyl)trimethoxysilane, and phenyltrimethoxysilane being preferred.

Other examples of useful second precursors include, without limitation, para-trifluoromethylterafluorophenyltrimethoxysilane, (tridecafluoro-1,1,2,2-tetrahydro-octyl)trimethoxysilane; second precursors having a ligand containing —OH, —SH, —NH$_2$ or aromatic nitrogen groups, such as 2-(trimethoxysilylethyl)pyridine, 3-aminopropyltrimethoxysilane, 3-mercaptopropyltrimethoxysilane and isocyanatopropyltrimethoxysilane, 2-(3,4-epoxycyclohexyl)ethyltrimethoxysilane and isocyanatopropyltrimethoxysilane, and second precursors with protected amine groups, such as trimethoxypropylbenzylcarbamate.

The sol-gel derived materials are obtained from an alkoxysilane precursor reaction medium, under acid or base sol-gel conditions, preferably base sol-gel conditions. In one aspect of the present invention, the alkoxysilane precursor reaction medium contains from about 100:00 vol:vol to about 10:90 vol:vol of the at least one first alkoxysilane precursor to the at least one second alkoxysilane precursor and, in one aspect, and from about 20:80 vol:vol to about 50:50 vol:vol first alkoxysilane precursor to second alkoxysilane precursor. In one aspect, the alkoxysilane precursor reaction medium contains 100% of the at least one first alkoxysilane precursor. The relative amounts of the at least one first alkoxysilane and the at least one second alkoxysilane precursors in the reaction medium will depend on the particular alkoxysilane precursors and the particular application for the resulting sol-gel derived material. The relative amounts will be readily determinable without undue experimentation.

The reaction medium includes a solvent for the alkoxysilane precursors. In some aspects, the solvent has a Dimoth-Reichart solvatochromism parameter (E$_T$) between 170-205 kJ/mol. Suitable solvents include, without limitation, tetrahydrofuran (THF), acetone, dichloromethane/THF mixtures containing at least 15% by vol. THF, and THF/acetonitrile mixtures containing at least 50% by vol. THF. Of these exemplary solvents, THF is preferred. The alkoxysilane precursors are preferably present in the reaction medium at between about 0.25 M and about 1 M, more preferably between about 0.4 M and about 0.8 M, most preferably about 0.5 M.

A catalytic solution comprising a catalyst and water is rapidly added to the reaction medium to catalyze the hydrolysis and condensation of the alkoxysilane precursors. Conditions for sol-gel reactions are well-known in the art and include the use of acid or base catalysts. Preferred conditions are those that use a base catalyst. Exemplary base catalysts include, without limitation, tetrabutyl ammonium fluoride (TBAF), fluoride salts, including but not limited to potassium fluoride, 1,5-diazabicyclo[4.3.0]non-5-ene (DBN), and alkylamines, including but not limited to propyl amines, of which TBAF is preferred. In one aspect, the concentration of TBAF in the catalytic solution is from about 0.00001 to about 0.002 M and in one is aspect, the concentration of TBAF in the catalytic solution is from about 0.001 to about 0.01 M As noted above, acid catalysts can be used to form sol-gel coatings, although acid catalysts are less preferred. Exemplary acid catalysts include, without limitation, any strong acid such as hydrochloric acid, phosphoric acid, sulfuric acid and the like.

In one aspect, water is present in the reaction medium at an amount so there is at least one half mole of water per mole of alkoxysilane groups in the alkoxysilane precursors. In one aspect, temperatures at polymerization can range from between the freezing point of the reaction medium up to the boiling point of the reaction medium. And in one aspect, the temperature range is from about 4° C. to about 50° C.

After gelation, the reaction product is preferably aged for an amount of time suitable to induce syneresis, which is the shrinkage of the gel that accompanies solvent evaporation. The aging drives off much, but not necessarily all, of the solvent. While aging times vary depending upon the catalyst and solvent used to form the gel, aging is typically carried out for about 5 minutes up to about 10 days, preferably from about 1 hour up to about 8 days and more preferably from about 5 to about 7 days. Aging is carried out at room temperature or elevated temperature (i.e., from about 18° C. up to about 60° C.), either in open atmosphere, under reduced pressure, or in a container or oven.

Solvent and catalyst extraction (i.e., rinsing) is carried out during or after the aging process. Preferred materials for extraction include, without limitation, any organic solvent of medium polarity, including, without limitation, THF, acetone, ethanol, and acetonitrile, either alone or in combination.

After rinsing, the sol-gel derived material is characterized by the presence of residual silanols. In one aspect, the silanol groups are derivatized with a reagent in an amount sufficient to stoichiometrially react with the residual silanols and prevent cross-linking that might otherwise occur between the residual silanol groups. Suitable derivatization reagents include, without limitation, reagents that have both one or more silanol-reactive groups and one or more non-reactive alkyl groups. The derivatization process results in the endcapping of the silanol-terminated polymers present within the sol-gel derived material with alkylsiloxy groups having the formula:

(3)

where each $R_3$ is independently an organic group as described above and w is an integer from 1 to 3.

One suitable class of derivatization reagents includes halosilanes, such as monohalosilane, dihalosilane and trihalosilane derivatization reagents that contain at least one halogen group and at least one alkyl group $R_1$, as described above. The halogen group can be any halogen, preferably Cl, Fl, I, or Br. Representative halosilanederivatization reagents include, without limitation, chlorosilanes, dichlorosilanes, fluorosilanes, difluorosilanes, bromosilanes, dibromosilanes, iodosilanes, and di-iodosilanes. Exemplary halosilanes suitable for use as derivatization reagents include, without limitation, cynanopropyldimethyl-chlorosilane, phenyldimethylchlorosilane, chloromethyldimethylchlorosilane, (trideca-fluoro-1,1,2,2-tertahydro-octyl)dimethyl-chlorosilane, n-octyldimethylchlorosilane, and n-octadecyldimethylchlorosilane. And in one aspect, the halosilane derivatization reagent is trimethyl chlorosilane.

Another suitable class of derivatization reagents includes silazanes or disilazanes. Any silazane with at least one reactive group and at least one alkyl group $R_1$, as described above can be used. A preferred disilazane is hexamethyldisilazane.

The sol-gel derived composition is preferably rinsed in any of the rinsing agents described above to remove excess derivatization reagent, and then dried. Drying can be carried out under any suitable conditions, but preferably in an oven, e.g., for about 2 hours at about 60 C to produce the sol-gel derived composition.

In some aspects, the compositions contain a plurality of flexibly tethered and interconnected organosiloxane particles having diameters on the nanometer scale. The organosiloxane nanoparticles form a porous matrix defined by a plurality of aromatically cross-linked organosiloxanes that create a porous structure.

And in some aspects, the resulting sol-gel compositions are hydrophobic, resistant to absorbing water, and absorb at least ten times the volume of acetone per mass of dry sol-gel derived composition.

Without being bound by theory, it is believed that swelling is derived from the morphology of interconnected organosilica particles that are cross-linked during the gel state to yield a nanoporous material or polymeric matrix. Upon drying the gel, tensile forces are generated by capillary-induced collapse of the polymeric matrix. This stored energy can be released as the matrix relaxes to an expanded state when a sorbate disrupts the inter-particle interactions holding the dried material in the collapsed state.

The sol-gel derived compositions can be used in any suitable form. In one aspect, the sol gel-derived composition is in a granular or a powder form. Depending upon the manner in which grinding of the sol-gel derived composition is carried out, the particle sizes may vary widely. The sol-gel derived compositions can be ground to small particle size (<10 um) without loss of their efficacy.

Powdered forms of the sol-gel derived composition are characterized by a high surface area, for example, in the range of about 800 m$^2$/g which allows for rapid and effective uptake of sebum and other fatty oils. Preferred powdered forms will have a high surface area (e.g., about 800 m$^2$/g) and an average particle size that is less than about 250 μm, for example, between about 50 to about 250 μm.

In one aspect, the sorbent capacity of the sol gel-derived composition for sebum is from about 1 to about 10 g/g and in one aspect, the sorbent capacity of the sol gel-derived composition for sebum is from about 3.5 to about 7 g/g. It is an advantage of the invention that the sol gel-derived composition sorbs, e.g., sequesters, the sebum and other oily compounds, while remaining dry to the user's touch FIG. 1 shows the capture of artificial sebum using powdered Osorb sorbent.

The compositions useful in accordance with the inventive method can be in any suitable form. In one aspect, the compositions are topical personal care compositions, home care compositions and the like and can include, for instance, creams, gels, lotions, emulsions, colloids, solutions, suspensions, ointments, milks, sprays, liquids, sticks, powders, spray-on formulations, brush-on formulations, cloths, wipes, and the like.

Non-limiting examples of topical personal care compositions can include, without limitation, body powder, shower gel, soap, body scrub, exfoliate, antidandruff formulation, antiperspirant composition, deodorant, shaving product, preshaving product, after shaving product, cleanser, skin gel, and rinse.

The compositions useful in accordance with the inventive method can be incorporated into any suitable vehicle. Non-limiting examples of suitable vehicles include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art.

The compositions useful in accordance with the inventive method can comprise one or more suitable desired optional components. For example, the composition can optionally include other active or inactive ingredients. The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, *Ginkgo biloba*, ginseng, and rosemary), antimicrobial agents, antioxidants (e.g., 131-IT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhi UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizol e tri siloxane, methylene bi s-benzotriazolyl tetramethylbutylphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide).

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, *althea officinalis* extract, apricot (*prunus armeniaca*) kernel oil, arginine, arginine aspartate, arnica montana extract, aspartic acid, avocado (*persea gratissima*) oil, barrier sphingolipids, butyl alcohol, beeswax, behenyl alcohol, beta-sitosterol, birch (*betula alba*) bark extract, borage (*Borago officinalis*) extract, butcherbroom (*ruscus aculeatus*) extract, butylene glycol, *Calendula officinalis* extract, *Calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sciarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (*Oenothera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*corylus americana*) nut oil, hazel (*corylus avellana*) nut oil, hexylene glycol, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*citrus medica limonum*) oil, linoleic acid, linolenic acid, macadamia ternifolia nut oil, maltitol, matricaria (*chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*citrus aurantium dulcis*) oil, palm (*Elaeis guineensis*) oil, palmitic acid, pantethine, panthenol, panthenyl ethyl ether, paraffin, PCA, peach (*prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*carthamus tinctorius*) oil, sage (*salvia officinalis*) oil, sandalwood (*santalum album*) oil, serine, serum protein, sesame (*Sesamum indicum*) oil, shea butter (*butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*cananga odorata*) oil.

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

In other non-limiting aspects, the compositions useful in accordance with the inventive method can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160 to 240 C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

Thickening agents, including thickener or gelling agents, include substances which that can increase the viscosity of a composition. Thickeners include those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

In accordance with one aspect of the invention, there is disclosed a method for removing sebum and other fatty oil by contacting a sebum or other fatty oil-containing substance with an effective amount of the personal care composition, home care composition or the like. It is a distinct advantage of the invention, that it is useful with a wide variety of substances, including without limitation cleansing or makeup-removing from the skin, the hair, including the scalp, and/or the mucous membranes (lips)

In one aspect, the inventive composition can be applied to a surface containing excess fatty oil, including without limitation excess sebum, and then the composition removed from the surface to remove the fatty oil. For example, in one embodiment the can be applied to a user's skin an then be rubbed off the skin to physically remove sebum or other fatty oil from the skin resulting in enhancement of tone to the skin. In another aspect, the inventive composition can be applied to a user's hair and then be brushed out of the hair to physically remove the sebum or other fatty oil from the hair resulting in enhancement of body to the hair.

In other aspects, the substance is an aqueous liquid or vapor.

The following examples are for the purpose of illustration only and are not intended to limit the scope of the claims, which are appended hereto.

EXAMPLES

Oily skin with a high sebum concentration was treated with an Osorb powder. The amount of sebum on the skin was measured using infrared spectroscopy done with attenuated total reflectance mode. There was a >95% decrease in sebum oil on the skin after application of the sol gel-derived composition.

We claim:
1. A method of making a sol-gel derived material, the method comprising:
combining

(a) at least one first alkoxysilane precursor having a formula:

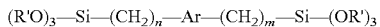
(R'O)₃—Si—(CH₂)ₙ—Ar—(CH₂)ₘ—Si—(OR')₃ where n and m are individually an integer from 1 to 8, Ar is a single-, fused-, or poly-aromatic ring, and each R' is independently a $C_1$ to $C_5$ alkyl group; and
(b) at least one second alkoxysilane precursor having a formula:

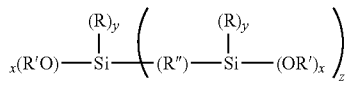

where x is 1; y is 2 or 3; z is 0 or 1; the total of x+y+z is 4; each R is independently an organic functional group, each an R' is independently a $C_1$ to $C_5$ alkyl group and R" is an organic bridging group; and
(c) a solvent, to form an alkoxysilane precursor reaction medium; and
catalyzing hydrolysis and condensation of the alkoxysilane precursors by adding to the reaction medium a catalytic solution comprising a catalyst and water, thereby obtaining the sol-gel derived material.

2. The method of claim 1, wherein the catalyst is a base catalyst.

3. The method of claim 2, wherein the base catalyst is selected from tetrabutylammonium fluoride (TBAF), potassium fluoride, 1,5-diazabicyclo[4.3.0]non-5-ene (DBN), and propylamines.

4. The method of claim 3, wherein the base catalyst is TBAF.

5. The method of claim 4, wherein the TBAF is present in the catalytic solution at a concentration of about 0.00001 to about 0.002 M.

6. The method of claim 4, wherein the TBAF is present in the catalytic solution at a concentration of about 0.001 to about 0.01 M.

7. The method of claim 1, further comprising, after formation of the sol-gel derived material, aging the reaction product.

8. The method of claim 7, further comprising rinsing during or after the aging process, to provide a sol-gel derived material characterized by residual silanol groups.

9. The method of claim 8, further comprising reacting the residual silanol groups with a derivatization reagent, resulting in end-capped silanol groups.

10. The method of claim 9, wherein the derivatization reagent is selected from halosilanes, silazanes, and disilazanes.

11. The method of claim 1, wherein y is 2 and z is 1, and R' is a methyl, ethyl, or propyl group.

12. The method of claim 1, wherein R comprises an unsubstituted or substituted straight-chain hydrocarbon group, branched-chain hydrocarbon group, cyclic hydrocarbon group, or aromatic hydrocarbon group.

13. The method of claim 1, wherein the plurality of alkylsiloxy groups have the formula:

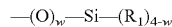
—(O)_w—Si—(R₁)_{4-w} where each $R_1$ is independently an organic group as described above and w is an integer from 1 to 3.

14. The method of claim 1 wherein the at least one first alkoxysilane precursor comprises a bis(trialkoxysilylalkyl)benzene.

15. The method of claim 14 where the at least one first alkoxysilane precursor comprises 1,4-bis(trimethoxysilylmethyl)benzene (BTMB), bis(triethoxysilylethyl)benzene (BTEB), or mixtures thereof.

16. A method of making a sol-gel derived material, the method comprising:
combining
(a) at least one first alkoxysilane precursor having a formula:

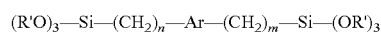
(R'O)₃—Si—(CH₂)ₙ—Ar—(CH₂)ₘ—Si—(OR')₃ where
n and m are individually an integer from 1 to 8, Ar is a single-, fused-, or poly-aromatic ring, and each R' is independently a $C_1$ to $C_5$ alkyl group; and
(b) at least one second alkoxysilane precursor having a formula:

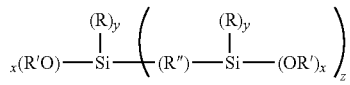

where x is 1; y is 2 or 3; z is 0 or 1; the total of x+y+z is 4; each R is independently an organic functional group, each an R' is independently a $C_1$ to $C_5$ alkyl group and R" is an organic bridging group; and
(c) a solvent, to form an alkoxysilane precursor reaction medium; and
catalyzing hydrolysis and condensation of the alkoxysilane precursors by adding to the reaction medium a catalytic solution comprising a base catalyst and water, thereby obtaining a reaction product;
aging the reaction product
thereby obtaining a sol-gel derived material having residual silanol groups; and
reacting the residual silanol groups with a derivatization reagent, thereby obtaining a sol-gel derived material having end-capped silanol groups.

17. The method of claim 16, wherein the base catalyst is tetrabutylammonium fluoride (TBAF).

18. The method of claim 16, wherein y is 2 and z is 1, and R' is a methyl, ethyl, or propyl group.

19. The method of claim 16, wherein R comprises an unsubstituted or substituted straight-chain hydrocarbon group, branched-chain hydrocarbon group, cyclic hydrocarbon group, or aromatic hydrocarbon group.

20. The method of claim 16, further comprising rinsing the reaction product during or after the aging process and before reacting the residual silanol groups with the derivatization reagent.

* * * * *